United States Patent
Souma et al.

(10) Patent No.: US 11,559,813 B2
(45) Date of Patent: Jan. 24, 2023

(54) SAFETY CABINET

(71) Applicant: Hitachi Industrial Equipment Systems Co., Ltd., Tokyo (JP)

(72) Inventors: Kenichi Souma, Tokyo (JP); Hirotoshi Sato, Tokyo (JP); Takeshi Kaneko, Tainai (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 242 days.

(21) Appl. No.: 16/957,274

(22) PCT Filed: Oct. 15, 2018

(86) PCT No.: PCT/JP2018/038288
§ 371 (c)(1),
(2) Date: Jun. 23, 2020

(87) PCT Pub. No.: WO2019/207818
PCT Pub. Date: Oct. 31, 2019

(65) Prior Publication Data
US 2021/0001341 A1    Jan. 7, 2021

(30) Foreign Application Priority Data

Apr. 24, 2018    (JP) .............................. JP2018-083421

(51) Int. Cl.
*B01L 7/00*    (2006.01)
*B01L 7/04*    (2010.01)

(52) U.S. Cl.
CPC ......... *B01L 7/04* (2013.01); *B01L 2300/1816* (2013.01); *B01L 2300/1822* (2013.01); *B01L 2300/1838* (2013.01); *B01L 2300/1883* (2013.01)

(58) Field of Classification Search
CPC ................. B01L 1/04; B01L 1/25; B01L 1/02
See application file for complete search history.

(56) References Cited

U.S. PATENT DOCUMENTS 6,878,177 B2 *    4/2005    Lohr .................. B01D 46/0036
422/123

FOREIGN PATENT DOCUMENTS

| CN | 105772135 A | * | 7/2016 | |
| CN | 106902899 A | * | 6/2017 | |
| CN | 206838110 U | | 1/2018 | |
| DE | 202013102927 U1 | * | 10/2013 | ............ A47J 39/003 |

(Continued)

OTHER PUBLICATIONS

Chinese-language Office Action issued in Chinese Application No. 201880085914.9 dated May 27, 2021 (nine (9) pages).

(Continued)

*Primary Examiner* — Christopher Adam Hixson
(74) *Attorney, Agent, or Firm* — Crowell & Moring LLP (57) ABSTRACT

Provided is a safety cabinet that reduces a temperature change between a storage environment temperature and a temperature in the safety cabinet to reduce damage to cultured microorganisms, cultured cells, or the like. The safety cabinet that includes a front panel and an operation opening in front of an operation space and an operation stage below the operation space and supplies purified air into the operation space from above, in which the operation stage is provided with a temperature-regulatable portion of which a temperature is regulatable.

13 Claims, 8 Drawing Sheets

(56) References Cited

FOREIGN PATENT DOCUMENTS

| | | | |
|---|---|---|---|
| EP | 0 487 028 A2 | 5/1992 | |
| JP | 52-140684 A | 11/1977 | |
| JP | 4-187077 A | 7/1992 | |
| JP | 5-256486 A | 10/1993 | |
| JP | 6-245685 A | 9/1994 | |
| JP | 7-103531 A | 4/1995 | |
| JP | 2001-25387 A | 1/2001 | |
| JP | 2005-300101 A | 10/2005 | |
| JP | 4387525 B2 | 12/2009 | |
| JP | 2011-24680 A | 2/2011 | |
| JP | 2017-78527 A | 4/2017 | |
| KR | 20090005619 | * 6/2009 | |
| WO | WO-2004114378 A1 * | 12/2004 | ............... B01L 1/04 |
| WO | WO-2006049609 A1 * | 5/2006 | ............... B01L 1/04 |
| WO | WO-2008018904 A2 * | 2/2008 | ............... B01L 1/00 |
| WO | WO-2017006983 A1 * | 1/2017 | ............... A61L 2/20 |

OTHER PUBLICATIONS

International Search Report (PCT/ISA/210) issued in PCT Application No. PCT/JP2018/038288 dated Jan. 15, 2019 with English translation (five (5) pages).
Japanese-language Written Opinion (PCT/ISA/237) issued in PCT Application No. PCT/JP2018/038288 dated Jan. 15, 2019 (five (5) pages).

* cited by examiner

SAFETY CABINET

TECHNICAL FIELD

The present invention relates to a safety cabinet that is used in research of the regenerative medicine, pathogens, and the like.

BACKGROUND ART

When cells or the like are handled in the regenerative medicine or the like where cells are cultured, a safety cabinet is used.

In a safety cabinet disclosed in Patent Document 1 as one example of the safety cabinet, a blowout HEPA filter is provided in an upper portion of an operation space, an openable and closable front shutter is provided in a front portion of the operation space, a rear side suction portion is provided in a rear portion wall, a front side suction portion is provided on a lower front side, air is uniformly supplied into the operation space from the blowout HEPA filter, and air is suctioned from the front side suction portion and the rear side suction portion of an operation pedestal forming a bottom surface of the operation space. Therefore, the air uniformly descends downward from above and thus the safety cabinet is purified.

CITATION LIST

Patent Document

Patent Document 1: JP 2017-78527 A

SUMMARY OF THE INVENTION

Problems to be Solved by the Invention

When the safety cabinet disclosed in Patent Document 1 is used, cells or the like are handled in the operation space; and thereby, it is possible to prevent the cells or the like from being contaminated and prevent the cells or the like from leaking from the operation space to an operator side.

Figure 11:
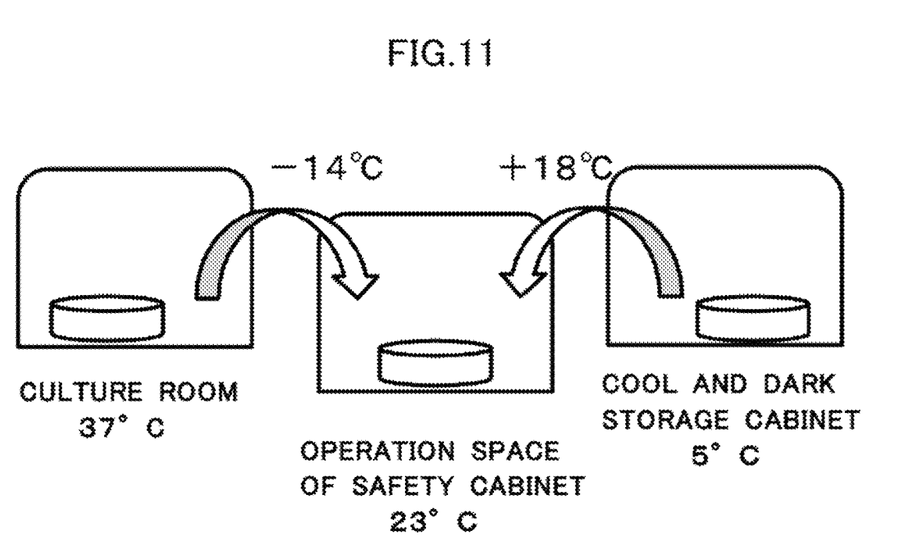
FIG. 11 is a view illustrating a relationship in temperature between a safety cabinet and other devices.

As illustrated in FIG. 11, normally, in many cases, the temperature of the operation space of the safety cabinet is set at a temperature of 20° C. to 25° C. (room temperature) that is suitable for an operation. On the other hand, in many cases, a culture medium container is kept from approximately 35° C. to 38° C. in a culture room, and in many cases, a cool and dark storage cabinet which reduces the proliferation rate is kept at approximately 5° C. As illustrated in the drawing, when a container stored at a predetermined temperature is moved into the operation space in the safety cabinet and an operation is performed, due to a difference between a storage environment temperature where the container has been stored up to now and a temperature in the safety cabinet, cells in culture may be damaged, and in some cases, the continuation of proper culture or the like may become difficult. A culture medium on a bottom portion of a petri dish has a thickness of approximately 10 mm, and when the petri dish is placed in the safety cabinet, the temperature of the culture medium is changed to a space temperature inside the safety cabinet. In culturing, the smaller a change in temperature, the less damage to cultured cells or cultured microorganisms.

An object of the present invention is to provide a safety cabinet that reduces a temperature change between a storage environment temperature and a temperature in the safety cabinet to reduce damage to cultured cells, cultured microorganisms, or the like.

Solutions to Problems

In order to solve the problem, as one example of a "safety cabinet" of the present invention, there is provided a safety cabinet that includes a front panel and an operation opening in front of an operation space and an operation stage below the operation space and supplies purified air into the operation space from above, in which the operation stage is provided with a temperature-regulatable portion of which a temperature is regulatable.

In addition, as another example of the "safety cabinet" of the present invention, there is provided a safety cabinet that includes a front panel and an operation opening in front of an operation space and an operation stage below the operation space and supplies purified air into the operation space from above, in which the operation stage is provided with a plurality of temperature-regulatable portions of which temperatures are individually settable.

Effects of the Invention

According to the present embodiment, since a temperature-regulatable portion of which a temperature is regulatable is provided in a safety cabinet, a temperature change between a storage environment temperature and a temperature in the safety cabinet is reduced; and thereby, it is possible to reduce damage to cultured cells, cultured microorganisms, or the like.

Tasks, configurations, and effects other than those described above become apparent from the description of the following embodiments.

MODE FOR CARRYING OUT THE INVENTION

Hereinbelow, embodiments of the present invention will be described with reference to the drawings. Incidentally, in

First Embodiment

Figure 1:
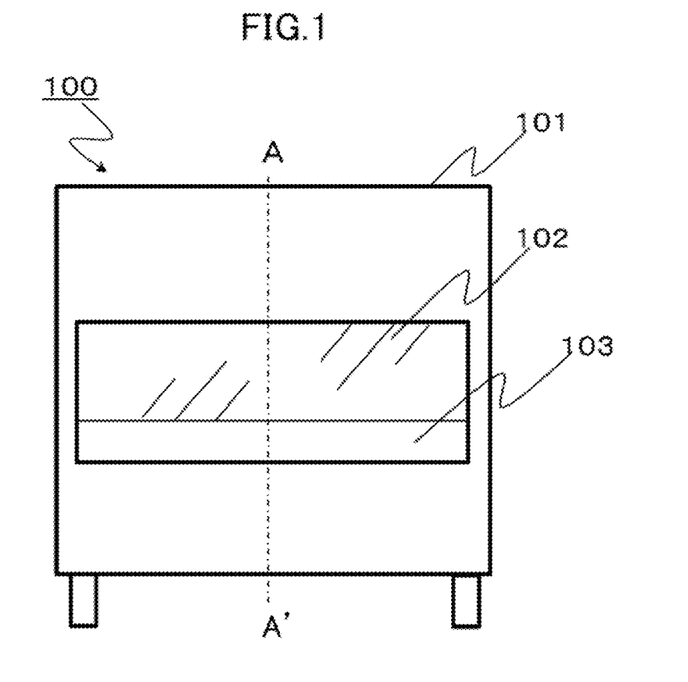
FIG. 1 is an example of an appearance front view illustrating a safety cabinet of a first embodiment.
Figure 2:
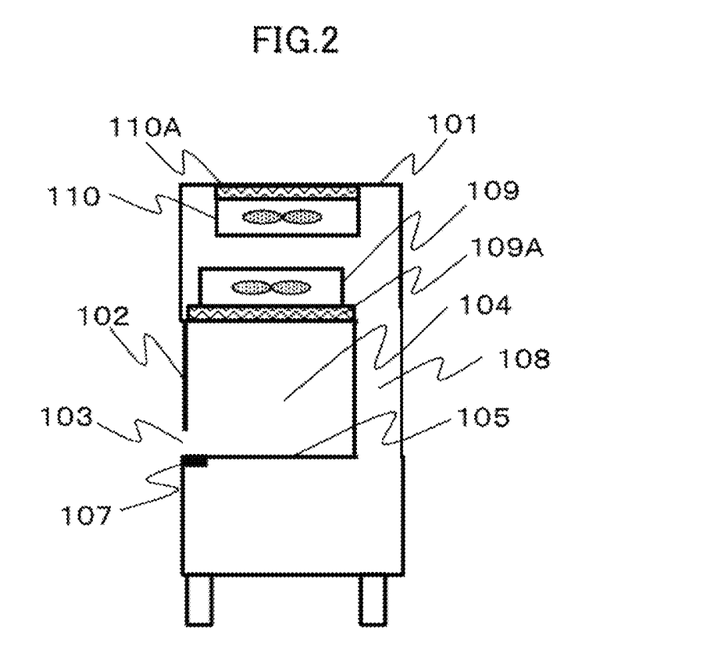
FIG. 2 is an example of a side cross-sectional view illustrating the safety cabinet of the first embodiment.

FIG. 1 illustrates a schematic front view of a safety cabinet. In addition, FIG. 2 illustrates a schematic side view of the safety cabinet when a cross section A-A' in FIG. 1 is seen from right.

An opening is provided in a central region of a housing 101 of a safety cabinet 100, and an operation space 104 is provided at the rear of the opening. A front panel 102 is provided on a front surface side of the operation space 104 so as to block an upper portion of the opening, and an operation opening 103 is provided below the front panel 102. An operator inserts the hands into the operation space 104 from the operation opening 103 to perform an operation. The front panel 102 is made of a transparent material such as glass, and the operator can see an operation through the front panel.

An operation stage 105 which is substantially flat is provided in a bottom surface of the operation space 104, and the operator performs an operation on the operation stage. An intake port 107 leading downward is provided on a front side of the operation stage 105 in the vicinity of the operation opening 103. The intake port 107 is formed as, for example, a slit that extends along the operation opening 103 in a rightward and leftward direction of the housing. A back flow path 108 leading from the intake port 107 to an upper portion of the housing is provided on a back surface side of the operation space 104.

A blowout side fan filter unit (FFU) 109 is provided above the operation space 104. The blowout side FFU 109 includes a fan that is rotated by a motor and a filter that removes microparticles, for example, a HEPA filter 109A, and blows out purified air, from which the microparticles have been removed, into the operation space 104. An exhaust side fan filter unit (FFU) 110 is provided in the upper portion of the housing 101 to remove microparticles from a part of air and exhaust the part of air outside the device through a filter, for example, a HEPA filter 110A.

Figure 3:
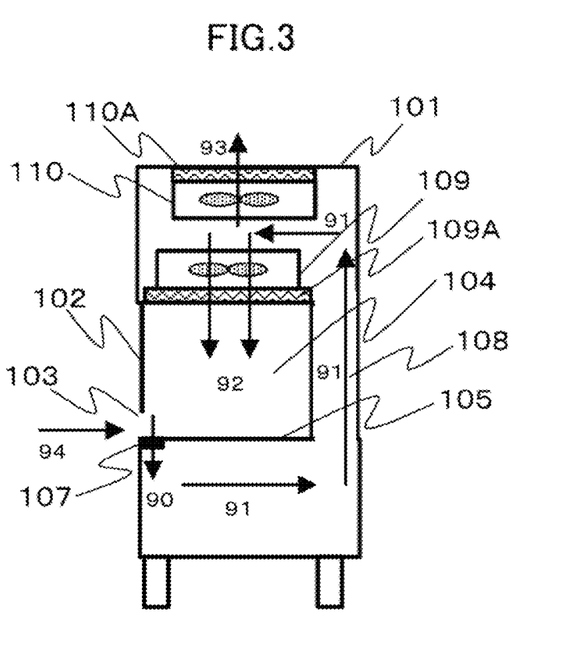
FIG. 3 is a view illustrating an air flow during operation of the safety cabinet in FIG. 2.

In FIG. 3, an air flow during operation of the safety cabinet is indicated by arrows. An air 90 which is suctioned from the intake port 107 on a front surface side of the operation stage 105 is blown, as denoted by reference sign 91, into the operation space 104 from the blowout side FFU 109 through a lower portion of the housing, the back flow path 108, and the upper portion of the housing. Since purified air from which the microparticles have been removed by the HEPA filter 109A of the blowout side FFU 109 is blown into the operation space 104, the operation space 104 is maintained in a purified state. In this case, when there is only an air flow, which is denoted by reference sign 92, into the operation space 104, air in the operation space leaks outside, which is a concern. For this reason, the exhaust side FFU 110 is provided to discharge a part of air outside through the HEPA filter 110A. Accordingly, the pressure in the operation space decreases, and an air flow 94 which is to be introduced from outside to inside through the operation opening 103 below the front panel 102 is generated. When the air flow 94 flows into the operation space as it is, the purity of the operation space deteriorates. However, the air volume of the air flow 92 which is blown out into the operation space from the blowout side FFU 109 and the air volume of an air flow 93 which is exhausted outside from the exhaust side FFU 110 are properly controlled, so that all of the air 94 flowing in from the operation opening 103 and the majority of the air 92 blown into the operation space are suctioned from the intake port 107. Therefore, an atmospheric barrier (air barrier) which prevents the air 94 from flowing into the operation space 104 from the operation opening 103 is formed by the air flow 92 which is blown out into the operation space 104. Accordingly, it is possible to realize an equilibrium state where the air from outside does not contaminate the operation space 104 and non-purified inside air does not leak outside.

Accordingly, even when the operator inserts the hands into the operation space 104 through the operation opening 103 to perform an operation, it is possible to realize the maintenance of the purity and the prevention of contamination.

Normally, in many cases, the temperature of the safety cabinet is not controlled, and the operation space in the safety cabinet is set at a room temperature (20° C. to 25° C.) that is suitable for an operation. On the other hand, in many cases, a culture medium container is kept from approximately 35° C. to 38° C. in a culture room, and in many cases, a cool and dark storage cabinet which reduces the proliferation rate is kept at approximately 5° C. When a container stored at a predetermined temperature is moved into the safety cabinet and an operation is performed, due to a difference between a storage environment temperature where the container has been stored up to now and a temperature in the safety cabinet, cells in culture may be damaged, and in some cases, the continuation of proper culture or the like may become difficult.

Figure 4:
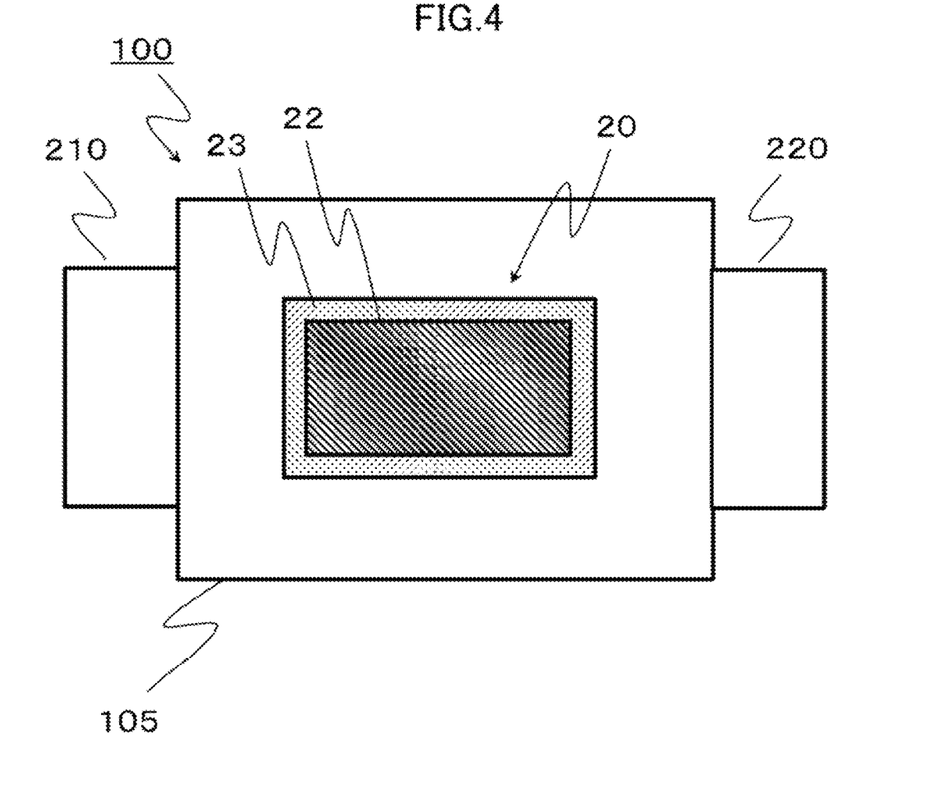
FIG. 4 is a top view illustrating an operation stage of the safety cabinet of the first embodiment.

FIG. 4 illustrates a characteristic configuration of the present embodiment. FIG. 4 is a top view of the operation stage of the safety cabinet when seen from the operation space. A temperature-regulatable portion 20 which can regulate the temperature with respect to a temperature outside the safety cabinet is provided in a part of the operation stage 105 of the safety cabinet 100. The temperature-regulatable portion 20 includes an operation panel 22 on which a specimen such as cells can be placed and an operation can be performed. It is desirable that the material of the operation panel 22 of the temperature-regulatable portion 20 is the same as the material of the operation stage 105. Normally, the operation stage 105 is made of a stainless steel, and thus the operation panel 22 can be made of a stainless steel. In this case, a heat insulating material 23 is provided between the operation panel 22 and the operation stage 105 so as to prevent the heat of the operation panel 22 from escaping to the operation stage 105.

In the drawing, reference sign 210 denotes a first pass box. The first pass box is connected to, for example, the culture room, and is kept at a high temperature of 37° C. Reference sign 220 denotes a second pass box. The second pass box is connected to, for example, a cool temperature storage cabinet, and is kept at a low temperature of 5° C.

Figure 5:
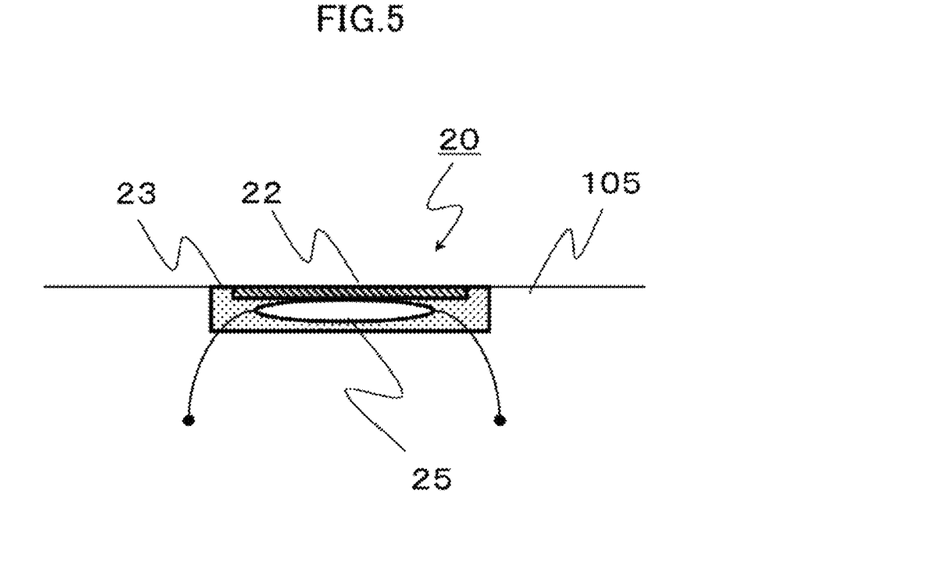
FIG. 5 is a view illustrating a configuration for regulating the temperature of a temperature-regulatable portion.

FIG. 5 illustrates a configuration for regulating the temperature of the operation panel 22 of the temperature-regulatable portion 20. An electrothermal conversion element 25 which can be electrically regulated is provided in the proximity of the operation panel 22 of the temperature-regulatable portion 20. When heating and cooling are performed, a Peltier element can be used as the electrothermal conversion element 25. In addition, when only heating is performed, a heater element may be used.

Figure 6:
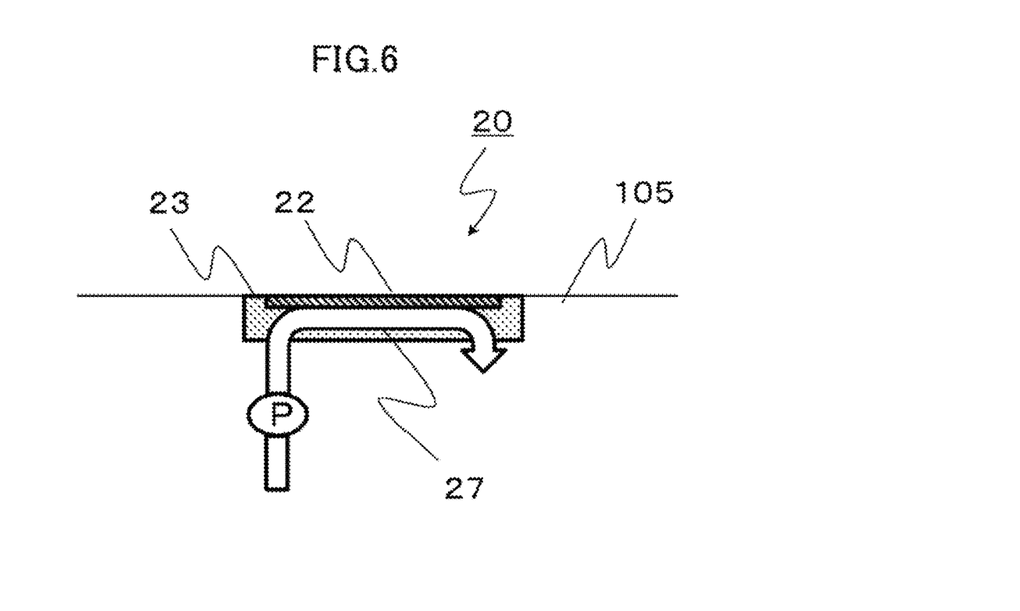
FIG. 6 is a view illustrating another configuration for regulating the temperature of the temperature-regulatable portion.

FIG. 6 illustrates another configuration for regulating the temperature. A pipe 27 through which a fluid flows is provided in the temperature-regulatable portion 20, and a temperature fluid is circulated therethrough by a pump. It is possible to regulate the temperature by changing the temperature of the fluid or changing the flow rate of the fluid.

Figure 7:
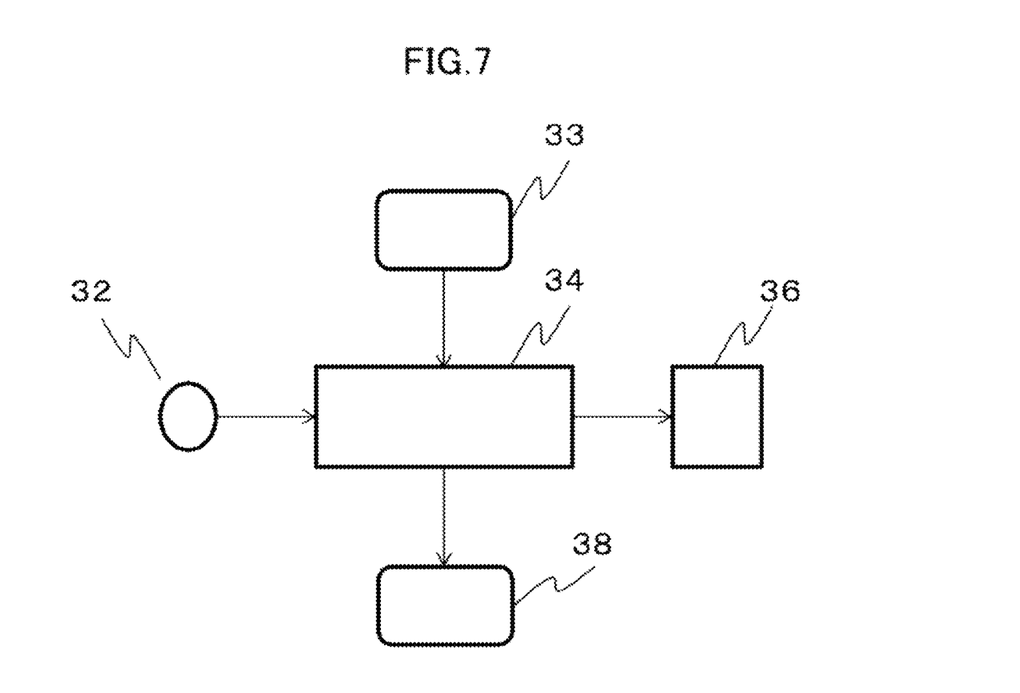
FIG. 7 is a block diagram illustrating a configuration of an electrical system of the safety cabinet of the first embodiment.

FIG. 7 illustrates one example of a block configuration diagram of an electrical system for performing temperature regulation. A temperature sensor 32 which measures the temperature of the temperature-regulatable portion 20 is provided, and measured temperature data is input to a control unit 34. The control unit 34 controls a temperature control element 36 such as a Peltier element according to the measured temperature, to control the temperature of the temperature-regulatable portion 20 to be constant. It is possible to randomly regulate the temperature of the temperature-regulatable portion 20 from a high temperature to a low temperature by setting a target temperature value using a temperature setting operation unit 33. It is possible to reduce a change in the temperature of cells and reduce damage to the cells by regulating the storage environment temperature to be substantially equal to the temperature of the operation space. In addition, when the temperature of the temperature-regulatable portion 20 is to be changed, it is possible to gradually raise or lower the temperature by regulating the amount of a change in temperature using the control unit 34. It is possible to prevent damage to the cells by avoiding the application of a rapid change in temperature to the cells.

A temperature display unit 38 which displays the temperature measured by the temperature sensor 32 is provided to display the temperature of the temperature-regulatable portion 20. The temperature display unit 38 may be disposed, for example, in a front surface of the safety cabinet, together with the temperature setting operation unit 33. It is desirable that the temperature of the temperature-regulatable portion 20 is always measured and monitored during operation of the safety cabinet.

Figure 8:
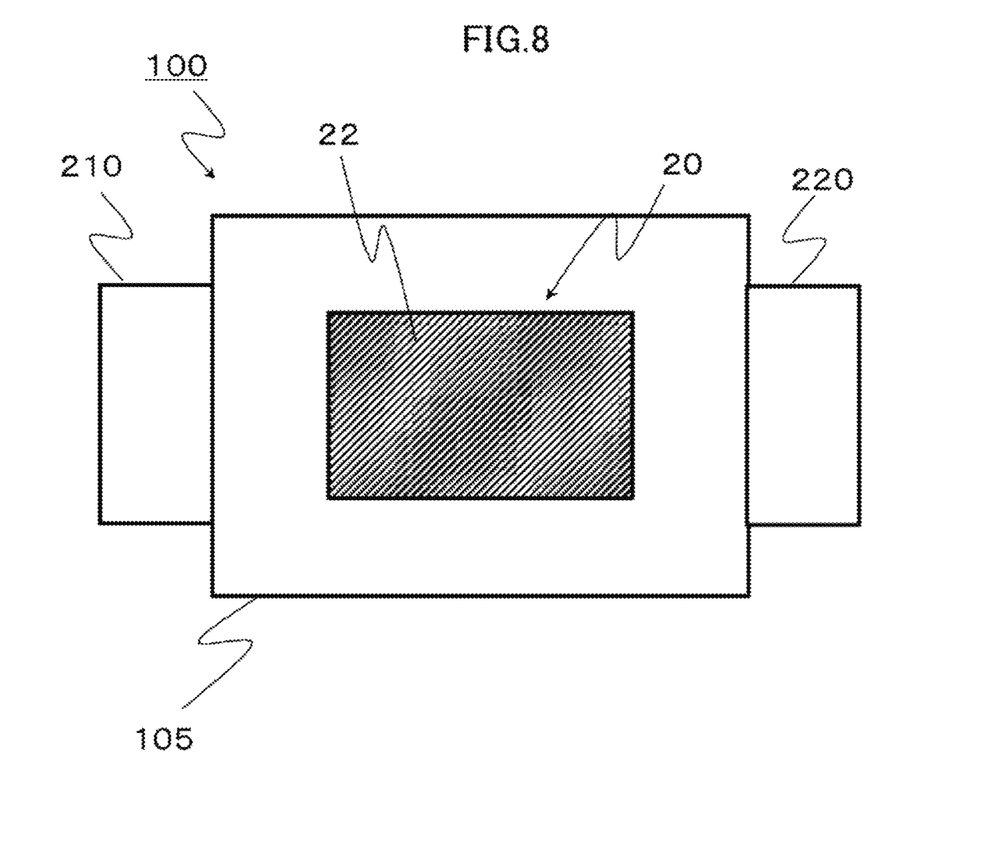
FIG. 8 is a top view illustrating a modification example of the operation stage of the safety cabinet of the first embodiment.

FIG. 8 illustrates a modification example of the temperature-regulatable portion 20. When a central operation region is to be always kept at a constant temperature, a material having a large heat capacity may be used as the material of the operation panel 22. It is possible to improve the uniformity of heat in a large region by using a material having a large heat capacity. For example, when a glass having a large heat capacity is used, since the glass also has the function of a heat insulating material, as illustrated in the drawing, the glass may be directly mounted on the operation stage 105 made of a stainless steel.

According to the present embodiment, since the temperature-regulatable portion of which the temperature is regulatable is provided on the operation stage of the safety cabinet, a temperature change between the storage environment temperature and the temperature in the safety cabinet is reduced; and thereby, it is possible to reduce damage to cultured cells, cultured microorganisms, or the like.

When the temperature of the temperature-regulatable portion is to be changed, the temperature is gradually raised or lowered, so that a rapid change in temperature is avoided. Therefore, it is possible to prevent damage to the cultured cells, the cultured microorganisms, or the like. In addition, after it is confirmed that the temperature of the temperature-regulatable portion has reached a predetermined temperature, the procedure can proceed to the next step of taking out a petri dish or the like; and thereby, it is possible to reduce a change in the temperature of the culture medium.

Second Embodiment

Figure 9:
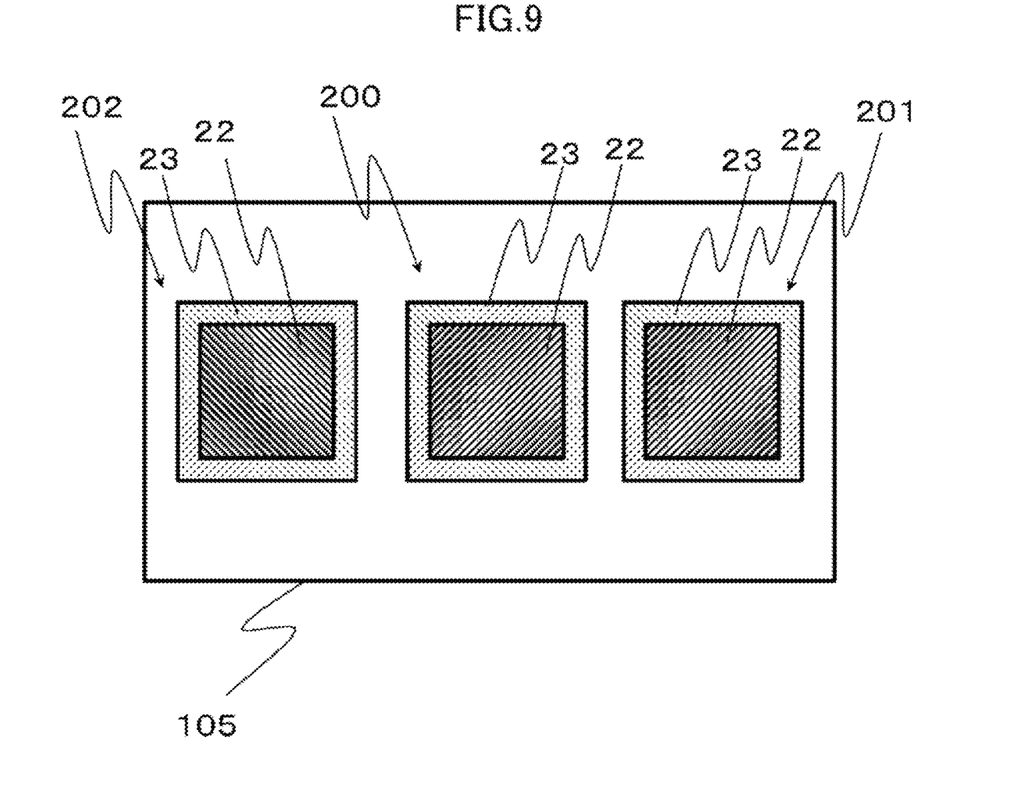
FIG. 9 is a top view illustrating one example of an operation stage of a safety cabinet of a second embodiment.

FIG. 9 illustrates one example of a safety cabinet of a second embodiment. In the second embodiment, a plurality of temperature-regulatable portions are provided on the operation stage.

As illustrated in the drawing, the plurality of temperature-regulatable portions are disposed on the operation stage 105, more specifically, in the example of the drawing, three temperature-regulatable portions 200, 201, and 202 are disposed at the center and on right and left sides of the operation stage. Then, the temperatures of the temperature-regulatable portions can be individually set; and thereby, it is possible to set the temperatures of cells, a drug solution, and the like to temperatures that are suitable therefor. In the drawing, at least one of the temperature-regulatable portions, for example, the temperature-regulatable portion 200 at the center may be an operation region.

As one example, when a right side of the safety cabinet is connected to the cool temperature storage cabinet via a low-temperature side pass box, the temperature of the temperature-regulatable portion 201 on the right side may be regulated to a low temperature. In this case, since a petri dish containing a specimen which is carried in from the external storage cabinet in a low temperature state can be placed on the temperature-regulatable portion 201 at a low temperature, and the temperature can be gradually raised, damage to a cultured tissue caused by a rapid thermal change can be prevented.

As another example, when the right side of the safety cabinet is connected to the cool temperature storage cabinet via the low-temperature side pass box, and a left side of the safety cabinet is connected to the culture room via a high-temperature side pass box, the temperature of the temperature-regulatable portion 201 on the right side is regulated to a low temperature, and the temperature of the temperature-regulatable portion 202 on the left side is regulated to a high temperature. Then, the temperature-regulatable portion 200 at the center may be an operation region at an intermediate temperature between the low and high temperatures. In this case, a thermal change of a specimen which is carried in from the external storage cabinet in a low temperature state or the culture room in a high temperature state is reduced; and thereby, damage to a cultured tissue caused by a rapid thermal change can be prevented.

As another example, when a movement direction of a specimen in the safety cabinet is determined in advance, for example, when the specimen is entered from the left side in the drawing, an operation is performed thereon at the center, and the specimen is released from the right side, the temperature of the temperature-regulatable portion 202 on the left side or the temperature of the temperature-regulatable portion 201 on the right side may be set to a temperature between a temperature before entry or after release and the temperature of the operation region at the center. Accordingly, it is possible to reduce the speed of a change in the temperature of the specimen.

The temperature-regulatable portion 201 and/or the temperature-regulatable portion 202 on the right side and/or on the left side may be storage regions for a drug such as a reagent. Even though the temperature of a specimen is constant, when the temperature of a reagent or the like to be added to the specimen is significantly different therefrom, a rapid change in temperature occurs due to the introduction of the reagent. It is possible to prevent the change in temperature by providing the storage region for the drug such as a reagent, of which the temperature is regulatable, and regulating the temperature of the storage region to be substantially equal to the temperature of the specimen.

The set temperatures of the temperature-regulatable portions in the operation region or other regions may be set in the safety cabinet itself. In addition, a temperature may be transmitted from the culture room (incubator) or the storage cabinet for a specimen via a network or the like, and the temperature of the temperature-regulatable portion may be automatically set to become a temperature close to the temperature.

Incidentally, in FIG. 9, the operation panel 22 is mounted on the operation stage 105 via the heat insulating material 23; however, as in the modification example of FIG. 8, the operating panel made of a material such as a glass having a large heat capacity may be directly mounted on the operation stage 105.

In addition, FIG. 9 illustrates the example where the three temperature-regulatable portions are provided; however, the number of the temperature-regulatable portions may be two or four or greater.

According to the present embodiment, since the plurality of temperature-regulatable portions are provided and the temperatures of the temperature-regulatable portions can be individually set, it is possible to set the temperatures of the temperature-regulatable portions to temperatures that are suitable for an operation, cultured cells, or a drug solution.

Third Embodiment

Figure 10:
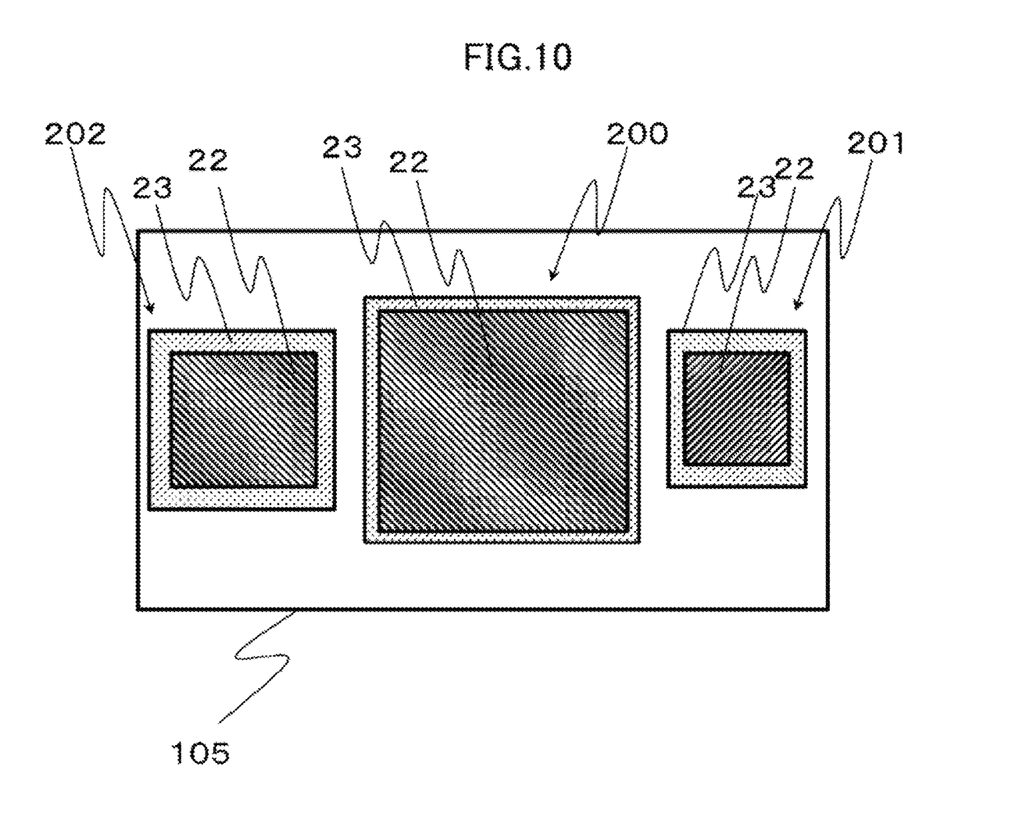
FIG. 10 is a top view illustrating one example of an operation stage of a safety cabinet of a third embodiment.

FIG. 10 illustrates one example of a safety cabinet of a third embodiment. In the third embodiment, the area of the temperature-regulatable portion 200 at the center which is an operation region is larger than the areas of the other temperature-regulatable portions 201 and 202. Normally, since an operation is performed in the central operation region, the temperature-regulatable portion 200 at the center is important and a specimen is present in the temperature-regulatable portion 200 for a long period of time. For this reason, the area of the temperature-regulatable portion 200 at the center is maximized; and thereby, it is possible to realize an improvement in operability and the stabilization of the temperature resulting from an increase in heat capacity.

In addition, as illustrated in the drawing, the area of the temperature-regulatable portion 201 or 202 on the right side or the left side may be set to an area according to the application.

REFERENCE SIGNS LIST

20 Temperature-regulatable portion
22 Operation panel
23 Heat insulating material
25 Electrothermal conversion element
27 Hot water pipe
32 Temperature sensor
33 Temperature setting operation unit
34 Control unit
36 Temperature control element
38 Temperature display unit
100 Safety cabinet
101 Housing
102 Front panel
103 Operation opening
104 Operation space
105 Operation stage
107 Intake port
108 Back flow path
109 Blowout side fan filter unit (FFU)
109A Blowout side HEPA filter
110 Exhaust side fan filter unit (FFU)
110A Exhaust side HEPA filter
200 Temperature-regulatable portion at center
201 Temperature-regulatable portion on right side
202 Temperature-regulatable portion on left side
210 Pass box on right side
220 Pass box on left side

The invention claimed is:

1. A safety cabinet comprising:
a front panel and an operation opening in front of an operation space and an operation stage below the operation space and supplies purified air into the operation space from above,
wherein the operation stage is provided with a temperature-regulatable portion of which a temperature is regulatable, and
wherein the temperature-regulatable portion includes an operation panel that is mounted on the operation stage via a heat insulating material.

2. The safety cabinet according to claim 1,
wherein the temperature-regulatable portion is an operation region where an operation is performed.

3. The safety cabinet according to claim 1,
wherein the temperature-regulatable portion includes an electrothermal conversion element.

4. The safety cabinet according to claim 3,
wherein the electrothermal conversion element is a Peltier element or a heater element.

5. The safety cabinet according to claim 1,
wherein the temperature-regulatable portion includes a pipe through which a temperature fluid flows.

6. The safety cabinet according to claim 3, further comprising:
a temperature sensor that measures a temperature of the temperature-regulatable portion; and
a control unit that controls the electrothermal conversion element such that the measured temperature becomes a set temperature.

7. The safety cabinet according to claim 6,
wherein the control unit gradually changes the temperature of the temperature-regulatable portion.

8. The safety cabinet according to claim 1, further comprising:
a temperature sensor that measures a temperature of the temperature-regulatable portion; and
a display unit that displays the temperature measured by the temperature sensor.

9. A safety cabinet that includes a front panel and an operation opening in front of an operation space and an operation stage below the operation space and supplies purified air into the operation space from above,
wherein the operation stage is provided with a plurality of temperature-regulatable portions of which temperatures are individually settable,
wherein one temperature-regulatable portion of the operation stage is used as an operation region and a set temperature of another temperature-regulatable portion is regulated to a temperature close to a temperature of a culture room or a storage cabinet for a specimen, and
wherein a temperature is transmitted from the culture room or the storage cabinet for the specimen via a network, and a temperature of the another temperature-regulatable portion is settable.

10. The safety cabinet according to claim 9,
wherein a temperature of another temperature-regulatable portion is gradually raisable or coolable.

11. The safety cabinet according to claim 9,
wherein one temperature-regulatable portion of the operation stage is used as an operation region and a set temperature of another temperature-regulatable portion is regulated to a temperature between a temperature of a culture room or a storage cabinet for a specimen and a temperature of the one temperature-regulatable portion.

12. The safety cabinet according to claim 9,
wherein an area of a temperature-regulatable portion at a center of the operation stage is larger than an area of another temperature-regulatable portion.

13. The safety cabinet according to claim 9,
wherein an operation region is a region on a center side among a plurality of regions.

* * * * *